United States Patent
Rothaemel et al.

(10) Patent No.: US 9,359,272 B2
(45) Date of Patent: Jun. 7, 2016

(54) PROCESS AND PLANT FOR PRODUCING C2-C4 OLEFINS FROM METHANOL AND/OR DIMETHYL ETHER WITH INCREASED YIELD

(75) Inventors: Martin Rothaemel, Frankfurt am Main (DE); Uwe Finck, Kjørsvikbugen (NO); Thomas Renner, Frankfurt am Main (DE); Henning Buchold, Hanau (DE)

(73) Assignee: Lurgi GmbH, Frankfurt am Main (DE)

( * ) Notice: Subject to any disclaimer, the term of this patent is extended or adjusted under 35 U.S.C. 154(b) by 1894 days.

(21) Appl. No.: 11/993,714

(22) PCT Filed: Jun. 23, 2006

(86) PCT No.: PCT/EP2006/006065
§ 371 (c)(1),
(2), (4) Date: May 11, 2010

(87) PCT Pub. No.: WO2006/136433
PCT Pub. Date: Dec. 28, 2006

(65) Prior Publication Data
US 2011/0319686 A1    Dec. 29, 2011

(30) Foreign Application Priority Data

Jun. 24, 2005 (DE) .......................... 10 2005 029 399

(51) Int. Cl.
  C07C 1/20       (2006.01)
  C07C 4/06       (2006.01)
(52) U.S. Cl.
  CPC ... C07C 1/20 (2013.01); C07C 4/06 (2013.01); Y02P 30/42 (2015.11)
(58) Field of Classification Search
  CPC ....................................................... C07C 1/20
  USPC ......... 585/312, 638, 639, 640, 650, 651, 652, 585/653, 310, 314, 324; 422/187
  See application file for complete search history.

(56) References Cited

U.S. PATENT DOCUMENTS 3,928,483 A * 12/1975 Chang et al. ................... 585/322
4,035,430 A *  7/1977 Dwyer et al. .................. 585/322

(Continued)

FOREIGN PATENT DOCUMENTS

| DE | 3524890 | 1/1986 |
| EP | 0145234 | 6/1985 |
| EP | 0882692 | 12/1998 |

OTHER PUBLICATIONS

Lide, CRC Handbook of Chemistry and Physics, D. R. Lide, ed., 93rd ed., 2013 internet version, available on-line at www.knovel.com.*

*Primary Examiner* — In Suk Bullock
*Assistant Examiner* — Sharon Pregler
(74) *Attorney, Agent, or Firm* — Pauly, Devries Smith & Deffner, LLC

(57) ABSTRACT

A process and a plant for producing $C_2$-$C_4$ olefins, in particular propylene, from an educt mixture containing steam as well as methanol vapor and/or dimethyl ether vapor. The educt mixture is reacted in at least one first reactor on a granular, form-selective zeolite catalyst to obtain a reaction mixture including low-molecular olefins and gasoline hydrocarbons, which in a first separating device is separated into a mixture rich in $C_2$-$C_4$ olefins, a mixture rich in $C_{5+}$ gasoline hydrocarbons, and an aqueous phase, wherein the mixture rich in gasoline hydrocarbons is mixed with an inert medium, the mixture thus obtained is reacted in at least one second reactor on a granular zeolite catalyst to obtain a product mixture including $C_2$-$C_4$ olefins, and this product mixture is recirculated to the first separating device, and wherein the mixture rich in $C_{5+}$ gasoline hydrocarbons is separated in a second separating device into a product stream containing $C_5$-$C_6$ hydrocarbons and a product stream containing $C_{7+}$ hydrocarbons, before being supplied to the second reactor, and only the product stream containing $C_{7+}$ hydrocarbons is supplied to the second reactor, whereas the product stream containing $C_5$-$C_6$ hydrocarbons together with the educt mixture is supplied to the at least one first reactor.

20 Claims, 1 Drawing Sheet

(56) References Cited

U.S. PATENT DOCUMENTS

| | | | |
|---|---|---|---|
| 4,404,414 A * | 9/1983 | Penick et al. | 585/469 |
| 4,433,188 A * | 2/1984 | Hoelderich et al. | 585/640 |
| 4,579,999 A * | 4/1986 | Gould et al. | 585/312 |
| 5,177,279 A * | 1/1993 | Harandi | 585/312 |
| 6,455,749 B1 * | 9/2002 | Vaughn | 585/640 |
| 2003/0078463 A1 * | 4/2003 | Martens et al. | 585/638 |
| 2004/0102667 A1 * | 5/2004 | Vora et al. | 585/324 |

* cited by examiner

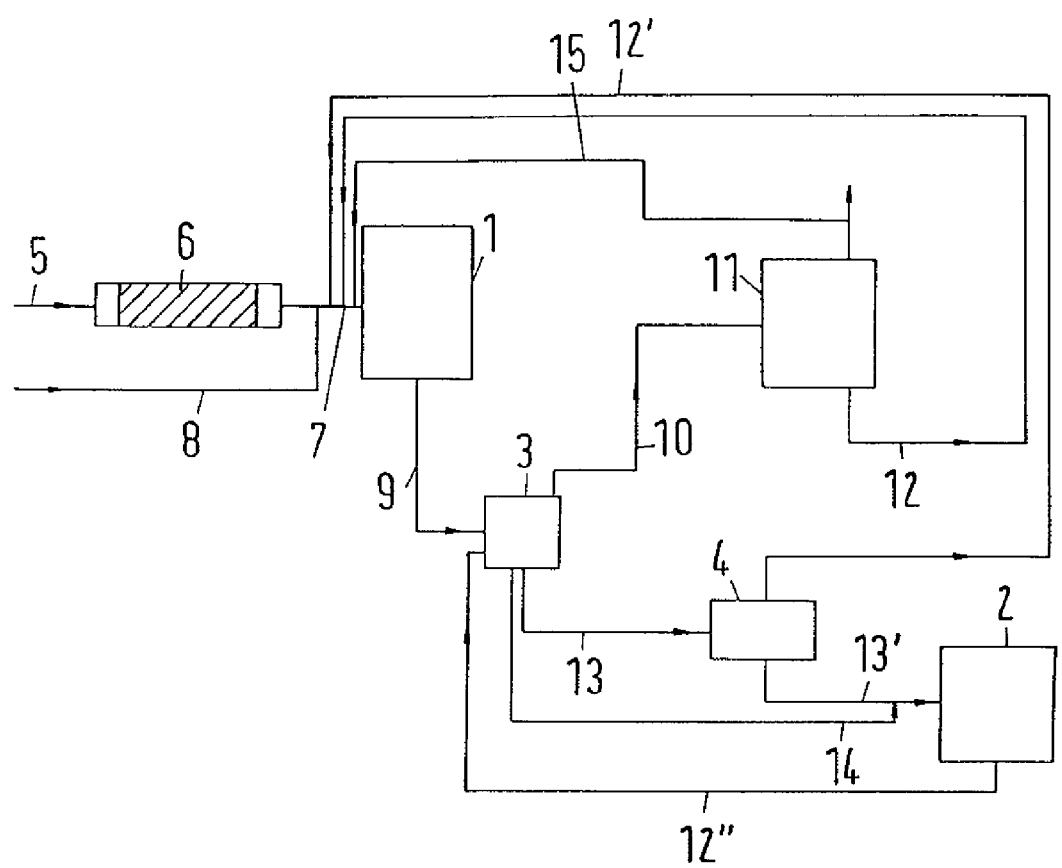

PROCESS AND PLANT FOR PRODUCING C2-C4 OLEFINS FROM METHANOL AND/OR DIMETHYL ETHER WITH INCREASED YIELD

PRIORITY

This application claims the benefit of German Patent Application No. DE 102005029399.9, filed Jun. 24, 2005, and International Patent Application Serial No. PCT/EP2006/006065, filed Jun. 23, 2006, each entitled "Process and Plant for Producing $C_2$-$C_4$ Olefins from Methanol and/or Dimethyl Ether with Increased Yield", wherein each of these applications is hereby incorporated by reference in its entirety.

FIELD OF THE INVENTION

The present invention relates to a process for producing $C_2$-$C_4$ olefins, in particular propylene, from an educt mixture containing steam as well as methanol vapor and/or dimethyl ether vapor.

BACKGROUND OF THE INVENTION

For producing low-molecular $C_2$-$C_4$ olefins, in particular propylene, from methanol and/or dimethyl ether, a multitude of processes are known to those skilled in the art, which are usually based on the reaction of an educt mixture containing steam as well as methanol vapor and/or dimethyl ether vapor on a form-selective zeolite catalyst.

DE 100 27 159 A1 discloses a process for producing propylene from methanol, in which first a vapor mixture containing dimethyl ether is produced from methanol vapor on a first catalyst, before the same is mixed with steam and is reacted in at least two sequentially operated reactors with catalyst beds of form-selective zeolite to obtain a product mixture containing propylene. Subsequently, the product mixture is processed in a separating device comprising several distillation columns, so that there is obtained a fraction rich in propylene with a propylene content of at least 95 vol-%, a fraction containing low-molecular hydrocarbons, which is recirculated to the catalyst beds, and a fraction rich in gasoline hydrocarbons, which is removed from the process. What is, however, disadvantageous in this process is the low yield of propylene, based on the total carbon content of the educt mixture, which among other things is due to the fact that the fraction rich in gasoline hydrocarbons is removed from the process.

From EP 0 882 692 B1 a process is known for producing $C_2$-$C_3$ olefins, in which a mixture of steam and methanol vapor and/or dimethyl ether vapor is reacted in a tubular reactor containing a zeolite catalyst at a temperature between 280 and 570° C. and a pressure between 0.1 and 0.9 bar to obtain a product mixture rich in olefins, which subsequently is separated in a separating device to obtain a $C_2$-$C_4$ olefin fraction with a propylene content of at least 40 wt-%, an aqueous fraction, a gaseous fraction, and a fraction containing $C_{5+}$ gasoline hydrocarbons. While the three first-mentioned fractions are withdrawn from the process, the product stream containing the $C_{5+}$ gasoline hydrocarbons is mixed with water, heated in a heater to a temperature of 380 to 700° C., and reacted to obtain $C_2$-$C_4$ olefins in a second reactor containing a zeolite catalyst, before the reaction products are recirculated to the separating device. The yields of $C_2$-$C_3$ olefins obtained with this process, although higher than the yields obtained with the process known from DE 100 27 159 A1, in which the fraction rich in gasoline hydrocarbons is removed from the process, likewise are in need of improvement. In addition, this process is known for its high costs, not least because of the isothermal procedure and the necessary vacuum operation in the tubular reactor.

What is needed is to provide a process for producing $C_2$-$C_4$ olefins, in particular propylene, from an educt mixture containing steam as well as methanol vapor and/or dimethyl ether vapor with a rather high yield.

SUMMARY OF THE INVENTION

In one aspect, the invention relates to a process for producing $C_2$-$C_4$ olefins from an educt mixture containing steam and methanol vapor and/or dimethyl ether vapor. The process includes reactive the educt mixture in at least one first reactor on a granular, form-selective zeolite catalyst to obtain a reaction mixture comprising low-molecular olefins and gasoline hydrocarbons, and separating the reaction mixture in a first separating device into a mixture rich in $C_2$-$C_4$ olefins, a mixture rich in $C_{5+}$ gasoline hydrocarbons, and an aqueous phase. Furthermore, in certain embodiments, the process includes mixing the mixture rich in gasoline hydrocarbons with an inert medium and reacting the resulting mixture in at least one second reactor on a granular zeolite catalyst to obtain a product mixture comprising $C_2$-$C_4$ olefins and recirculating the product mixture to the first separating device. In addition, before being supplied to the second reactor, the mixture rich in $C_{5+}$ gasoline hydrocarbons can be separated in a second separating device into a product stream containing $C_5$-$C_6$ hydrocarbons and a product stream containing $C_7$, hydrocarbons and only the product stream containing $C_{7+}$ hydrocarbons is supplied to the second reactor, whereas the product stream containing $C_5$-$C_6$ hydrocarbons is supplied to the at least one first reactor together with the educt mixture.

An additional aspect of the invention relates to a plant for producing $C_2$-$C_4$ olefins, in particular propylene, from an educt mixture containing steam as well as methanol vapor and/or dimethyl ether vapor. The plant typically includes at least one first reactor and at least one second reactor, each of which contains a granular form-selective zeolite catalyst. The plant further includes a first separating device for separating the reaction mixture obtained in the first reactor and a second separating device which is adapted to separate a mixture rich in $C_{5+}$ gasoline hydrocarbons into a product stream containing $C_5$-$C_6$ hydrocarbons and a product stream containing $C_{7+}$ hydrocarbons before supplying the same to the second reactor. The plant also includes a return line which leads from the second reactor to the first separating device.

The above summary of the present invention is not intended to describe each discussed embodiment of the present invention. This is the purpose of the figures and the detailed description that follows.

BRIEF DESCRIPTION OF THE DRAWING

The invention may be more completely understood in connection with the following drawing, in which:

FIG. 1 schematically shows a plant which can be used for performing the process of the invention.

While the invention is susceptible to various modifications and alternative forms, specifics thereof have been shown by way of example and drawing, and will be described in detail. It should be understood, however, that the invention is not limited to the particular embodiments described. On the contrary, the intention is to cover modifications, equivalents, and alternatives falling within the spirit and scope of the invention.

DETAILED DESCRIPTION OF THE INVENTION

The present invention relates to a process for producing $C_2$-$C_4$ olefins, in particular propylene, from an educt mixture containing steam as well as methanol vapor and/or dimethyl ether vapor, in which the educt mixture is reacted in at least one first reactor on a granular, form-selective zeolite catalyst to obtain a reaction mixture comprising low-molecular olefins and gasoline hydrocarbons, which in a first separating device is separated into a mixture rich in $C_2$-$C_4$ olefins, a mixture rich in $C_{5+}$ gasoline hydrocarbons, and an aqueous phase, wherein the mixture rich in gasoline hydrocarbons is mixed with an inert medium, the mixture thus obtained is reacted in at least one second reactor on a granular zeolite catalyst to obtain a product mixture comprising $C_2$-$C_4$ olefins, and this product mixture is recirculated to the first separating device. The present invention furthermore relates to a plant suitable for performing the process.

In accordance with the present invention, the yield of $C_2$-$C_4$ olefins in a process for producing $C_2$-$C_4$ olefins, in particular propylene, from an educt mixture containing steam as well as methanol vapor and/or dimethyl ether vapor is increased significantly without increasing the operating costs, when the fraction containing $C_{5+}$ gasoline hydrocarbons, which in the first separating device was separated from the reaction mixture obtained upon reaction of the educt mixture in the first reactor, is first of all separated in a second separating device into a product stream comprising $C_5$-$C_6$ hydrocarbons as well as a product stream comprising $C_{7+}$ hydrocarbons, and only the product stream containing the $C_{7+}$ hydrocarbons is reacted in the second reactor, whereas the product stream containing the $C_5$-$C_6$ hydrocarbons together with the educt mixture is supplied to the at least one first reactor and is again reacted there to obtain low-molecular olefins. Both the product stream containing $C_5$-$C_6$ hydrocarbons and the product stream containing $C_{7+}$ hydrocarbons contains unexpectedly high amounts of compounds which can be reacted on a form-selective zeolite catalyst to obtain $C_2$-$C_4$ olefins. While the last-mentioned fraction of $C_{7+}$ hydrocarbons includes significant amounts of aromatics, which react with methanol and/or dimethyl ether by forming alkylaromatic compounds, and therefore cannot be reacted together with the educt mixture containing methanol and/or dimethyl ether, the first-mentioned fraction of $C_5$-$C_6$ hydrocarbons is substantially free from aromatics and therefore can be used in the first reactor without a risk of undesired side reactions.

In the second separating device, a product stream containing $C_7$+. hydrocarbons, which comprises 10 to 30 wt-% of $C_{7+}$ paraffins, 40 to 70 wt-% of aromatics, 5 to 20 wt-% of naphthenes, 5 to 25 wt-% of $C_{7+}$ olefins as well as less than 20 wt-% of C6-hydrocarbons, is preferably separated from the mixture rich in $C_{5+}$ gasoline hydrocarbons, as these compositions have a high content of compounds which can be reacted on a zeolite catalyst to obtain $C_2$-$C_4$ olefins and in particular propylene. Particularly good results are obtained when the $C_{7+}$ product stream separated in the second separating device contains 15 to 25 wt-% of $C_{7+}$ paraffins, 40 to 50 wt-% of aromatics, 15 to 20 wt-% of naphthenes, 15 to 25 wt-% of $C_{7+}$ olefins as well as less than 10 wt-% of C6-hydrocarbons. Quite particularly preferably, the content of C6-hydrocarbons, i.e. hydrocarbons with a chain length of 6 C atoms or less, in the $C_{7+}$ product stream is less than 5 wt-%.

In accordance with the invention, it is possible to separate in the second separating device a product stream containing $C_5$-$C_6$ hydrocarbons, which contains less than 5 wt-% of aromatics, preferably less than 2.5 wt-% of aromatics, and particularly preferably less than 1 wt-% of aromatics. These compositions also have a high content of compounds which can be reacted on a zeolite catalyst to obtain $C_2$-$C_4$ olefins and in particular propylene. In addition, the low content of aromatics ensures that in the subsequent reaction of the $C_5$-$C_6$ product stream in the first reactor no undesired side reactions, in particular no alkylation reactions with methanol, do occur.

The second separating device can be designed in any way known to those skilled in the art, if it is adapted to separate a mixture rich in $C_{5+}$ gasoline hydrocarbons into a product stream containing $C_5$-$C_6$ hydrocarbons and a product stream containing $C_{7+}$ hydrocarbons. Merely by way of example, reference should be made to separating devices operating by distillation, by adsorption, thermally or by means of membranes, particularly good results being obtained by means of distillation columns.

As inert medium to be supplied to the product stream containing $C_{7+}$ hydrocarbons, which was formed in the second separating device, water, nitrogen and/or butane turned out to be particularly useful, water being particularly preferred for this purpose.

In accordance with the invention, the educt mixture supplied to the first reactor can contain 0 to 100 wt-% of methanol and 100 to 0 wt-% of dimethyl ether in addition to steam, based on its steam-free content. Gas mixtures containing methanol and or dimethyl ether can for instance be produced in a manner known per se by partial conversion of methanol on a granular alumina catalyst, the reaction preferably being performed at a temperature between 200 and 350° C.

Preferably, the first reactor constitutes a fixed bed reactor, tubular reactor, stationary fluidized-bed reactor or circulating fluidized-bed reactor. In the second case, the reactor preferably includes a plurality of axially arranged tubes, which for instance have a length between 1 m and 5 m as well as an inside diameter of 20 mm to 50 mm.

To achieve a rather high conversion of the educt mixture, the same is passed through two or more sequentially operated first reactors, in accordance with a particular embodiment of the present invention. For this embodiment, in particular more than two, preferably three, series-connected fixed bed reactors each with a form-selective zeolite catalyst turned out to be particularly useful, part of the educt mixture from the prereactor being introduced into the first fixed bed reactor and the product mixture from the fixed bed reactor upstream of each further reactor together with a partial stream of the educt mixture from the prereactor being introduced into each further fixed bed reactor.

Similar conversions of the educt mixture are obtained when as an alternative to the aforementioned embodiment the educt mixture is passed only through a first reactor, in which at least two sequentially operated catalyst stages are provided. In this case, the individual catalyst stages preferably are arranged one below the other and are traversed by the educt mixture from the top to the bottom. Here as well, the educt mixture is distributed from the prereactor to the individual catalyst stages.

In principle, all zeolite catalysts known to those skilled in the art as suitable for the conversion of methanol and/or dimethyl ether into $C_2$-$C_4$ olefins can be used in the at least one first reactor, wherein alumosilicate zeolite of the pentasile type and particularly preferably ZSM-5 turned out to be particularly useful. For optimizing the yield, it is furthermore preferred to supply at least one inert stream, particularly preferably steam, and at least one stream containing hydrocarbons, to the reactor, i.e. the first reactor or the first reactor stage.

In order to decrease the operating costs of the process, it is proposed in accordance with a development of the invention to perform the conversion in the at least one first reactor and/or in the at least one second reactor adiabatically. Alternatively, an isothermal procedure is possible, although less preferred, in the aforementioned reactors, which as compared to the adiabatic procedure, would, however, lead to higher process costs.

Good yields in the at least one first reactor are obtained in particular, when an educt mixture with a weight ratio of water to methanol equivalent of 0.25:1 to 6:1 is supplied thereto. If the reactor comprises a plurality of catalyst stages, this ratio applies to the inlet of each catalyst stage. According to equation 2 with $CH_3OH \rightarrow CH_3$—O—$CH_3+H_2O$, one "methanol equivalent" corresponds to half a mole of dimethyl ether (DME). In addition, the educt mixture is preferably reacted in the first reactor at a temperature of 300 to 600° C. and/or at a pressure of 0.5 to 5 bar(a).

For separating the reaction mixture withdrawn from the first reactor, there can be used any separating device known to those skilled in the art, which can be used for separating a mixture rich in $C_2$-$C_4$ olefins from a mixture rich in $C_{5+}$ gasoline hydrocarbons, for instance separating devices operating by distillation, by adsorption, thermally or by means of membranes. Particularly good results are obtained when the first separating device constitutes a cooling device and the reaction mixture withdrawn from the first reactor is cooled therein to a temperature of 10 to 80° C.

In accordance with a further preferred embodiment of the present invention, the mixture rich in $C_2$-$C_4$ olefins withdrawn from the first separating device is supplied to a third separating device, in which the aforementioned mixture is separated into a $C_4$-$C_5$ olefin stream and a $C_{3-}$ olefin stream. This provides for the recirculation of the $C_4$-$C_5$ olefin stream to the first reactor, whereby the total yield of the process can further be increased. From the $C_{3-}$ olefin stream, propylene can easily be recovered, with a high purity for instance by distillation. Preferably, the olefins left upon separation of propylene from the $C_{3-}$ olefin stream are also recirculated to the first reactor.

In the second reactor, the same catalysts as in the first reactor can be used in principle, alumosilicate zeolite of the pentasile type and in particular ZSM-5 being preferred. In particular, good yields are obtained in the second reactor when a mixture with a water/hydrocarbon ratio of 0.1:1 to 3:1 and preferably at least 1:1 is supplied thereto. In addition, the product stream in the second reactor is preferably reacted at a temperature of 380 to 700° C. and particularly preferably of 400 to 600° C. and/or preferably at a pressure of 0.2 to 5 bar(a) and particularly preferably of 1.0 to 2.5 bar(a).

Another aspect of the present invention is a plant for producing $C_2$-$C_4$ olefins, in particular propylene, from an educt mixture containing steam as well as methanol vapor and/or dimethyl ether vapor, which plant is particularly useful for performing the processes described herein. In accordance with the invention, the plant comprises at least one first reactor and at least one second reactor, both reactors containing each a granular form-selective zeolite catalyst, as well as a first separating device for separating the reaction mixture obtained in the first reactor, wherein the plant furthermore includes a second separating device which is adapted to separate a mixture rich in $C_{5+}$ gasoline hydrocarbons into a product stream containing $C_5$-$C_6$ hydrocarbons and a product stream containing $C_{7+}$ hydrocarbons before supplying the same to a second reactor, and wherein a return line leads from the second reactor to the first separating device.

In accordance with an embodiment of the present invention, a third separating device for separating the mixture rich in $C_2$-$C_4$ olefins, which was withdrawn from the first separating device, into a $C_4$-$C_5$ olefin stream and a $C_{3-}$ olefin stream is provided downstream of the first separating device, wherein the third separating device comprises at least one distillation column.

In another embodiment of the invention it is proposed to provide in the plant a return line leading from the third separating device to the first reactor, in order to recirculate the mixture rich in $C_4$-$C_5$ olefins, which was withdrawn from the third separating device, into the first reactor.

The plant as shown in FIG. 1 comprises a first reactor 1 and a second reactor 2, each of which contains a catalyst on the basis of form-selective zeolite, preferably an alumosilicate zeolite of the pentasile type and particularly preferably ZSM-5. While the first reactor 1 preferably constitutes a fixed bed reactor, tubular reactor, stationary fluidized-bed reactor or circulating fluidized-bed reactor, the catalyst in the second reactor 2 preferably is arranged as fixed bed. Furthermore, the plant comprises a first separating device 3 designed as cooler as well as a second separating device 4.

During operation of the plant, methanol supplied via the methanol supply line 5 is heated in a heat exchanger (not shown) to a temperature of preferably 200 to 350° C. and is evaporated thereby, before the methanol vapor is at least partly reacted in the prereactor 6 on a suitable dehydrating catalyst, e.g alumina, to obtain dimethyl ether and water. Via gas line 8, steam is supplied to the methanol/dimethyl ether mixture withdrawn from the prereactor via line 7, and the mixture thus obtained is introduced into the first reactor 1. Preferably, the inlet temperature of the educt mixture into the first reactor 1 is between 350 and 500° C., the weight ratio of water to methanol equivalent in the educt mixture is between 0.25:1 and 6:1, and the pressure in the first reactor 1 is between 0.5 and 5.0 bar(a). Inside the catalyst layers of the first reactor, the temperatures preferably lie in the range between 300 and 600° C.

As an alternative to the one-stage configuration of the first reactor 1 as shown in FIG. 1, the same can also consist of two or more sequentially operated reaction stages, which can both constitute separately designed reactors and catalyst beds disposed one above the other in one reactor. In this case, the product from the prereactor 6 is distributed on the individual stages, whereas all other inlet streams are completely introduced into the first reaction stage. Furthermore, it is also possible to exclusively use methanol or dimethyl ether in combination with steam as educt in the first reactor 1 instead of a steam/methanol/dimethyl ether mixture.

Via line 9, the reaction mixture formed in the first reactor 1, which mainly consists of $C_2$-$C_4$ olefins, $C_{5+}$ gasoline hydrocarbons and steam, is withdrawn from the first reactor 1 and supplied to the first separating device 3, in which the reaction mixture is cooled to a temperature between 10 and 80° C., so that a condensate rich in water, an organic liquid phase rich in $C_{5+}$ gasoline hydrocarbons, and a gas phase substantially consisting of $C_2$-$C_4$ olefins are obtained.

From the first separating device 3, the fraction rich in $C_2$-$C_4$ olefins is supplied via line 10 to a third separating device 11, in which it is separated into a $C_4$-$C_5$ olefin stream and a $C_{3-}$ olefin stream. While the first-mentioned olefin stream is recirculated to the first reactor 1 via the return line 12 and the methanol/dimethyl ether discharge line 7, propylene and propane are separated from the $C_{3-}$ olefin stream via a further separating device (not shown), and the residual $C_{2-}$ stream free from propylene is recirculated to the first reactor via line 15. The further purification of the propylene separated from the $C_{3-}$ olefin stream can be achieved by means of processes known from the prior art.

Via line 13, the organic phase obtained in the first separating device 3, which substantially consists of $C_{5+}$ gasoline hydrocarbons, is introduced into the second separating device 4, which constitutes a distillation column and in which this phase is separated into a $C_5$-$C_6$ hydrocarbon stream and a $C_{7+}$ hydrocarbon stream. The first-mentioned hydrocarbon stream is recirculated to the first reactor 1 via the return line 12' and the methanol/dimethyl ether discharge line 7, whereas the $C_{7+}$ hydrocarbon stream is first passed through a heater (not shown), in which the mixture of $C_{7+}$ hydrocarbons and water is heated to a temperature of preferably 380 to 600° C., via line 13', to which water withdrawn as liquid condensate from the first separating device 3 is supplied via line 14, and is subsequently introduced into the second reactor 2, in which the aforementioned mixture is reacted on a granular zeolite catalyst to obtain a product mixture comprising $C_2$-$C_4$ olefins. Via return line 12", this product mixture is withdrawn from the second reactor 2 and recirculated to the first separating device 3.

To avoid too high concentrations of inert substances in the process loop, a small amount of the $C_2$-$C_4$ olefins, the $C_5$-$C_6$ hydrocarbons and the $C_{7+}$ hydrocarbons is continuously discharged from the process circuit (not shown).

The invention will be explained below with reference to an example demonstrating the invention, but not limiting the same.

Example 1

In a plant such as shown in FIG. 1, 2.23 kg/h of a mixture of 8.7 wt-% of methanol vapor, 32.9 wt-% of dimethyl ether vapor and 58.3 wt-% of steam were supplied to the first reactor 1 via lines 5, 7, 8; 0.75 kg/h of the $C_4$-$C_5$ olefin stream withdrawn from the third separating device via lines 12, 7; 0.13 kg/h of ethylene via lines 15, 7, and via lines 12', 7; 0.18 kg/h of the $C_5$-$C_6$ hydrocarbon stream withdrawn from the second separating device, the inlet temperature of the mixture introduced into reactor 1 being 459° C. and the pressure at the inlet of reactor 1 being 2.15 bar(a).

Via line 9, the reaction mixture was withdrawn from reactor 1 and introduced into the first separating device 3 constituting a cooler, in which the reaction mixture was cooled to 24° C. 0.33 kg/h of a fraction rich in $C_{5+}$ gasoline hydrocarbons, based on 1 kg of catalyst in the first reactor 1, were withdrawn from the bottom of the separating device 3 and were separated in the second separating device 4 into a product stream containing $C_5$-$C_6$ hydrocarbons and a product stream containing $C_{7+}$ hydrocarbons, wherein the product stream containing the $C_{7+}$ hydrocarbons had the following composition:
- 18.5 wt-% of $C_{7+}$ paraffins,
- 42.4 wt-% of aromatics,
- 18.7 wt-% of naphthenes,
- 19.2 wt-% of $C_{7+}$ olefins, and
- less than 0.3 wt-% of $C_6$ hydrocarbons and the product stream containing $C_5$-$C_6$ hydrocarbons had the following composition:
- 32.6 wt-% of $C_{7-}$ paraffins,
- 0.2 wt-% of aromatics,
- 14.3 wt-% of naphthenes, and
- 52.9 wt-% of $C_{7-}$ olefins.

While the product stream containing $C_5$-$C_6$ hydrocarbons was recirculated to the first reactor 1 via lines 12', 7, the product stream containing $C_{7+}$ hydrocarbons with a mass flow rate of 3 kg/h was mixed with 1.5 kg/h of steam, based on one kilogram of catalyst in the second reactor 2, the mixture thus obtained was heated and with an inlet temperature of about 480° C. introduced into the second reactor 2, which was operated at a pressure of 1.3 bar(a). The product withdrawn from reactor 2 was recirculated to the first separating device 3 via line 12" with a mass flow rate of 0.095 kg/h.

In addition, a mixture rich in $C_2$-$C_4$ olefins was withdrawn from the first separating device and supplied via line 10 to a third separating device 11, in which this stream was separated into a $C_4$-$C_5$ olefin stream and a C3-olefin stream. From the C3-olefin stream, propylene was recovered with a yield of 69.3%.

The present invention should not be considered limited to the particular examples described above, but rather should be understood to cover all aspects of the invention as fairly set out in the attached claims. Various modifications, equivalent processes, as well as numerous structures to which the present invention may be applicable will be readily apparent to those of skill in the art to which the present invention is directed upon review of the present specification. The claims are intended to cover such modifications and devices.

The above specification provides a complete description of the structure and use of the invention. Since many of the embodiments of the invention can be made without parting from the spirit and scope of the invention, the invention resides in the claims.

What is claimed is:

1. A process for producing C2-C4 olefins from a mixture containing steam and methanol vapor and/or dimethyl ether vapor, the process comprising:
   (i) reacting the mixture in at least one first reactor on a granular, form-selective zeolite catalyst to obtain a reaction mixture comprising low-molecular olefins and gasoline hydrocarbons;
   (ii) separating the reaction mixture in a first separating device into a mixture rich in C2-C4 olefins, a mixture rich in C5+ gasoline hydrocarbons, and an aqueous phase;
   (iii) separating the mixture rich in C5+ gasoline hydrocarbons in a second separating device into a product stream containing C5-C6 hydrocarbons and a product stream containing C7+ hydrocarbons, wherein the product stream containing C7+ hydrocarbons contains 40 to 70 wt-% of aromatics;
   (iv) mixing the product stream containing C7+ hydrocarbons with an inert medium, and supplying only the stream containing C7+ hydrocarbons and inert medium to a second reactor and reacting on a granular zeolite catalyst to obtain a product mixture comprising C2-C4 olefins; wherein the second reactor operates at a temperature of 380 to 700° C.; and
   (v) recirculating the product stream containing $C_5$-$C_6$ hydrocarbons to the first reactor.

2. The process of claim 1, where the product stream containing $C_{7+}$ hydrocarbons, which was separated in the second separating device, contains 10 to 30 wt-% of $C_{7+}$ paraffins, 5 to 20 wt-% of naphthenes, 5 to 25 wt-% of $C_{7+}$ olefins as well as less than 20 wt-% of C6- hydrocarbons.

3. The process of claim 1, where the product stream containing $C_{7+}$ hydrocarbons, which was separated in the second separating device, contains 15 to 25 wt-% of $C_{7+}$ paraffins, 40 to 50 wt-% of aromatics, 15 to 20 wt-% of naphthenes, 15 to 25 wt-% of $C_{7+}$ olefins and less than 5 wt-% of $C_{6-}$ hydrocarbons.

4. The process of claim 1, where the product stream containing $C_5$-$C_6$ hydrocarbons, which was separated in the second separating device, contains less than 5 wt-% of aromatics.

5. The process of claim 1, where the product stream containing $C_5$-$C_6$ hydrocarbons, which was separated in the second separating device, contains less than 2.5 wt-% of aromatics.

6. The process of claim 1, where the product stream containing $C_5$-$C_6$ hydrocarbons, which was separated in the second separating device, contains less than 1 wt-% of aromatics.

7. The process of claim 1, where the second separating device comprises a distillation column.

8. The process of claim 1, where before being supplied to the second reactor, the mixture rich in $C_{7+}$ gasoline hydrocarbons is mixed with water, nitrogen and/or butane as inert medium.

9. The process of claim 1, where the at least one first reactor comprises a fixed bed reactor, tubular reactor, stationary fluidized-bed reactor or circulating fluidized-bed reactor.

10. The process of claim 1, where the first reactor comprises two or more sequentially operated reactors or at least two sequentially operated catalyst stages.

11. The process of claim 1, where the catalyst in the first reactor or second reactor is a pentasil aluminosilicate-zeolite.

12. The process of claim 11, where the catalyst is ZSM-5.

13. The process of claim 1, where the reaction in the at least one first reactor or in the at least one second reactor is performed adiabatically.

14. The process of claim 1, where the weight ratio of water to methanol equivalent, based on all methanol inlet streams, of the mixture supplied to the first reactor is adjusted to 0.25:1 to 6:1, and the mixture is reacted in the first reactor at a temperature of 300 to 600° C. and/or at a pressure of 0.5 to 5 bar(a).

15. The process of claim 1, where the first separating device is a cooling device in which the reaction mixture is cooled to a temperature of 10 to 80° C.

16. The process of claim 1, where the mixture rich in $C_2$-$C_4$ olefins, which was obtained in the first separating device, is supplied to a third separating device in which the mixture is separated into a $C_4$-$C_5$ olefin stream and a $C_{3-}$ olefin stream.

17. The process of claim 16, where the $C_4$-$C_5$ olefin stream is recirculated to the first reactor.

18. The process of claim 17, where propylene is separated from the $C_{3-}$ olefin stream and the remaining olefins are recirculated to the first reactor.

19. The process of claim 1, where the water/hydrocarbon ratio of the product stream supplied to the second reactor is adjusted to 0.1:1 to 3:1, and the product stream in the second reactor is reacted at a temperature of 380 to 700° C. and at a pressure of 0.2 to 5 bar(a).

20. The process of claim 1, where the water/hydrocarbon ratio of the product stream supplied to the second reactor is adjusted to at least 1:1, and the product stream in the second reactor is reacted at a temperature of 400 to 600° C. and at a pressure of 1.0 to 2.5 bar(a).

\* \* \* \* \*